(12) United States Patent
Sanchez Ramos

(10) Patent No.: US 11,635,556 B2
(45) Date of Patent: Apr. 25, 2023

(54) BLOCKING ELEMENT OF SHORT WAVELENGTHS IN LED-TYPE LIGHT SOURCES

(71) Applicant: UNIVERSIDAD COMPLUTENSE DE MADRID, Madrid (ES)

(72) Inventor: Celia Sanchez Ramos, Madrid (ES)

(73) Assignee: UNIVERSIDAD COMPLUTENSE DE MADRID, Madrid (ES)

( * ) Notice: Subject to any disclaimer, the term of this patent is extended or adjusted under 35 U.S.C. 154(b) by 0 days.

(21) Appl. No.: 17/331,351

(22) Filed: May 26, 2021

(65) Prior Publication Data

US 2022/0091317 A1    Mar. 24, 2022

Related U.S. Application Data

(62) Division of application No. 14/426,115, filed as application No. PCT/ES2013/070222 on Apr. 5, 2013, now Pat. No. 11,035,990.

(30) Foreign Application Priority Data

Dec. 21, 2012 (ES) .............................. ES201201268

(51) Int. Cl.
| | |
|---|---|
| *G02B 5/22* | (2006.01) |
| *G01J 1/42* | (2006.01) |
| *G02B 19/00* | (2006.01) |
| *H01L 33/44* | (2010.01) |
| *A61F 2/16* | (2006.01) |

(Continued)

(52) U.S. Cl.
CPC ................ *G02B 5/22* (2013.01); *A61B 5/68* (2013.01); *G01J 1/0219* (2013.01); *G01J 1/0233* (2013.01); *G01J 1/4204* (2013.01); *G01J 1/429* (2013.01); *G02B 5/223* (2013.01); *G02B 19/0066* (2013.01); *H04N 9/64* (2013.01); *A61B 5/1118* (2013.01); *A61F 2002/16965* (2015.04); *G01J 9/00* (2013.01); *G02B 5/201* (2013.01); *G09F 9/33* (2013.01); *G09F 9/335* (2021.05);

(Continued)

(58) Field of Classification Search
CPC ...... G02B 5/22; G02B 5/223; G02B 19/0066; G02B 5/201; A61B 5/68; A61B 5/1118; G01J 1/0219; G01J 1/0233; G01J 1/4204; G01J 1/429; G01J 9/00; H04N 9/64; G09G 2320/06; G09G 2320/08; H01L 33/44; G09F 9/33; G09F 9/335; A61F 2002/16965; G03C 1/815
See application file for complete search history.

(56) References Cited

U.S. PATENT DOCUMENTS

| | | | | |
|---|---|---|---|---|
| 4,878,748 A | * | 11/1989 | Johansen | ................ G02C 7/104 351/44 |
| 4,952,046 A | * | 8/1990 | Stephens | ................ G02C 7/104 351/159.6 |

(Continued)

FOREIGN PATENT DOCUMENTS

WO    WO-2013032076 A1 *    3/2013    ........... G03H 1/0005

*Primary Examiner* — Douglas M Wilson
(74) *Attorney, Agent, or Firm* — ArentFox Schiff LLP

(57) ABSTRACT

Method, product and blocking element of short wavelengths in LED-type light sources consisting of a substrate with a pigment distributed on its surface and, in that said pigment has an optical density such that it allows the selective absorption of short wavelengths between 380 nm and 500 nm in a range between 1 and 99%.

5 Claims, 18 Drawing Sheets

(51) Int. Cl.
*A61B 5/00* (2006.01)
*G01J 1/02* (2006.01)
*H04N 9/64* (2023.01)
*A61B 5/11* (2006.01)
*G02B 5/20* (2006.01)
*G09F 9/33* (2006.01)
*G01J 9/00* (2006.01)

(52) U.S. Cl.
CPC ..... *G09G 2320/06* (2013.01); *G09G 2320/08* (2013.01); *H01L 33/44* (2013.01)

(56) References Cited

U.S. PATENT DOCUMENTS

| | | | | |
|---|---|---|---|---|
| 5,365,068 A * | 11/1994 | Dickerson | ............. | G01J 1/4204 340/600 |
| 5,841,507 A * | 11/1998 | Barnes | ................... | G02C 7/104 351/49 |
| 6,820,014 B2 * | 11/2004 | Ferrero | ................... | A61Q 17/04 250/372 |
| 6,893,127 B2 * | 5/2005 | Reichow | ................... | G02C 7/104 351/44 |
| 7,033,577 B2 * | 4/2006 | Dueva-Koganov | .... | G01N 21/33 600/407 |
| 7,066,596 B2 * | 6/2006 | Ishak | ..................... | G02C 7/108 351/44 |
| 8,210,678 B1 * | 7/2012 | Farwig | ..................... | G02B 5/22 351/159.65 |
| 8,360,574 B2 * | 1/2013 | Ishak | ..................... | G02C 7/104 351/159.63 |
| 8,570,648 B2 * | 10/2013 | Sanchez | ................ | G02B 5/208 128/858 |
| 8,793,212 B2 * | 7/2014 | McGuire | ................... | G06N 5/00 706/62 |
| 9,377,569 B2 * | 6/2016 | Ishak | ..................... | G02C 7/102 |
| 10,347,163 B1 | 7/2019 | Herf et al. | | |
| 10,551,637 B2 * | 2/2020 | Ishak | ........................ | G02C 7/10 |
| 11,035,990 B2 | 6/2021 | Sanchez Ramos | | |
| 2004/0075810 A1 * | 4/2004 | Duha | ..................... | G02C 7/104 351/159.24 |
| 2004/0149921 A1 * | 8/2004 | Smyk | ..................... | A61B 5/445 250/372 |
| 2005/0018131 A1 * | 1/2005 | Ishak | ..................... | G02C 7/108 351/159.62 |
| 2005/0041299 A1 * | 2/2005 | Gallas | ..................... | G02C 7/108 359/642 |
| 2007/0019287 A1 * | 1/2007 | Wong | ..................... | G02F 1/0126 359/361 |
| 2007/0073487 A1 * | 3/2007 | Albright | ................. | G01J 1/429 702/3 |
| 2009/0147215 A1 * | 6/2009 | Howell | ..................... | G01J 1/0271 250/206 |
| 2010/0282266 A1 * | 11/2010 | Sanchez | ................. | G02B 5/223 623/4.1 |
| 2011/0191272 A1 * | 8/2011 | McGuire | ................... | G06N 5/00 706/11 |
| 2012/0075577 A1 * | 3/2012 | Ishak | ..................... | G02C 7/10 351/159.6 |
| 2018/0113327 A1 * | 4/2018 | Ishak | ..................... | G02C 7/108 |
| 2021/0325584 A1 | 10/2021 | Sanchez Ramos et al. | | |

* cited by examiner

BLOCKING ELEMENT OF SHORT WAVELENGTHS IN LED-TYPE LIGHT SOURCES

CROSS-REFERENCE TO RELATED APPLICATIONS

This application is a Divisional of U.S. patent application Ser. No. 14/426,115, filed Mar. 4, 2015, which is a National Stage entry of International Application No. PCT/ES2013/070222, filed Apr. 5, 2013, which claims priority to Spanish Patent Application No. P201201268, filed Dec. 21, 2012. The disclosures of the prior applications are hereby incorporated in their entirety by reference.

FIELD OF THE INVENTION

In general, the present invention falls within the field of optics and, in particular, relates to a blocking element of short wavelengths in LED-type light sources (light-emitter diodes).

STATE OF THE ART

The electromagnetic spectrum (EME) is the energy distribution of the whole of the electromagnetic waves that a substance emits (emission spectrum) or absorbs (absorption spectrum). The EME includes a wide range of radiation, from that of lower wavelength such as gamma rays and x-rays, passing through ultraviolet radiation, light and infra-red rays, to the electromagnetic waves with longer wavelength, such as radio waves.

The light spectrum is the region of the electromagnetic spectrum that human eye is able to perceive. Electromagnetic radiation in this range of wavelengths is also called 'visible' or simply light. There are no exact limits in the visible spectrum; a typical human eye responds to wavelengths from 380 nm to 780 nm, although the eye adapted to the dark can see over a greater range, ranging from 360 nm to 830 nm.

The retina auto-protects itself from the short wavelengths in two ways: with a heterogeneous distribution of the photo-receptors in such a way that photo-receptors, sensitive to the short wavelengths, do not exist in the macular depression and by the action of yellow pigments existing in the same area that also perform a protective action. In addition, the crystalline increases its proportion of yellow chromophores with age.

These natural protections of the human eye against the shortest wavelengths (the crystalline and those of the retina) can find themselves seriously affected by certain pathologies and/or surgical interventions, even exclusively over time.

Some techniques have been developed to protect healthy eyes, cataract operated eyes, and eyes in neuro-degenerative retina process from short wavelengths:

Apply filters to the human eyes as a therapeutic and preventive measure to substitute and/or improve the natural protection.

Since the middle of the 90's, intraocular lenses provided with a yellow filter have been implanted on cataract operated eyes. This alternative involves a surgical procedure with all its obvious risks and difficulties. There also exists a large number of people operated from cataracts to which a transparent intraocular lens has been implanted to substitute the inner substance of the crystalline that does not have the necessary yellow pigmentation protection. In these cases, it is necessary to complement the artificial crystalline, which is exempt of yellow pigmentation, with the insertion of a yellow pigmentation support system.

A blocking element of the short wavelengths is a device designed to separate, pass or delete a group of objects or things of the total mixture. The blocking elements are designed for the selection of a particular range of wavelengths of light. The mechanism is always subtractive, consists of blocking of wavelengths, allowing the passage of other wavelengths.

There are different types of filters applied to the human eye on the market. For instance, the patent application WO 98/44380 describes a filter applied in a contact lens that does not cover the whole of said contact lens, understanding the whole as iris area, pupil area and the contact lens body, this fact being fundamental for avoiding irregularities in vision. On the other hand, the document WO 91/04717 describes intraocular lenses for treating of AMD which is not the object of the present invention.

It is also known the fact of using yellow filters in ophthalmic lenses, for example through the document GB 1 480 492.

The yellow filter can be used in multiple applications, as shown by the documents located in the current state of the art.

The document DE 358 948 describes a yellow filter applied to an electrical lighting device, but combined with a second red-colored filter, which moves away from the inventive concept described in the present invention.

The document ES 1 046 793 U describes an external support device of different lighting filters, with different colors, which moves away from the inventive concept of the present invention which lies in a unique blocking element of short wavelengths, integrated in a given material, to eliminate the short wavelengths from the visible light spectrum before it reaches the user due to pernicious effects produced by the high energy of this light range, aim that, evidently, is not achieved with this document.

The document WO 90/05321 describes a filter with a series of technical features but that absolutely defines a pathophysiological application and in addition, the filter described in the patent application WO 90/05321 is not homogeneous in its absorbance and may produce unwanted effects.

Dr. Celia Sanchez-Ramos is the inventor of the patents ES2247946, ES2257976, ES2281301, ES2281303, ES2289957, ES2296552, ES2298089, ES2303484 and ES2312284. However, although these documents are referred to the issue of ambient light, especially the short wavelengths on the spectrum from 380 to 500 nm, none of these documents explains the problem derived from the mass and daily use of screens primarily based on LED technology in its different variants, like OLED, LCD-LED, AMOLED, among other cutting-edge technologies for smartphones, electronic tablets, laptops and televisions, projectors and in general any screen with LED technology and/or LED backlight.

A practical example of this type of LED technology displays is in document US20120162156 of Apple Inc., which describes how it is internally that known commercially as Retina® display and implemented in various products marketed by Apple, as the MacBook Pro®, iPad® 2, or iPhone® 5. Although said document describes extensively how it is emitted the light by the LEDs (more specifically, those known as organic LEDs or OLED), at no time the presence of any medium or element to limit radiation emitted to the user of the device is considered.

FIG. 1 shows the different graphs of emission for products currently marketed within the visible range.

It is clear that today any particular user spends an average of 4-8 hours a day, or more, in front of LED-type displays, i.e. receiving an emission of short wavelengths at a usually very small distance (on the order of 30-50 cm), which negatively affects the eye and human vision. This problem is described in the state of the art in [Behar-Cohen et al. '*Light-emitting diodes (LED) for domestic lighting: Any risks for the eye?*' Progress in Retinal and Eye Research 30 (2011) 239-257].

Said document, in the conclusions thereof, emphasizes the need to evaluate the potential toxicity of the light emitted by the LEDs, depending on the various devices available on the market so that efficient recommendations can be made to the domestic light manufacturers, due to the increased presence of LED-type lighting for indoor environments. However, this document does not commit to a solution to combine the evolution of the LED technique with a risk-free everyday use. That is, this document advocates, directly, the limitation and legal regulation of light emissions, without proposing any kind of solution for the already marketed products.

Another document that describes the associated problems in [Cajochen et al. '*Evening exposure to a light-emitting diodes (LED)-backlight computer screen affects circadian physiology and cognitive performance*', Journal of Applied Physiology 110: 1432-1438, 2011, first published 17 Mar. 2011] where the need to adapt the light emission to the sleep cycle is described.

This document, however, indicates that the potential toxicity of the LED-type displays is unknown and that, in any case, their associated problems can be reduced by reducing the light intensity.

The technical problem that underlies is the reduction of risk in the eye damage due to the intensive use of LED-type displays. From the document by Behar-Cohen, it is known to which type of damages the human eye is exposed, but in its conclusions, the most obvious way is used, which is to limit the use of that type of screens and force manufacturers, in a generic way, to restrict their emissions within a specific range. However, it leaves unanswered precisely how to reduce this type of emissions in the simplest way as possible, not only at the manufacturing step, which is not always possible, easy or simple, but also with the products currently existing on the market.

DESCRIPTION OF THE INVENTION

On the basis of the technical problem described, and with the aim that the blocking element of emissions object of the invention does not have to be the same in all cases and also has to be easy to implement by any user and not only by experts.

To provide a solution to the technical problem in an aspect of the invention, the blocking element of short wavelengths in LED-type light sources characterized in that it consists of a substrate with a pigment distributed on its surface, and in that said pigment has an optical density such that it allows the selective absorption of short wavelengths between 380 nm and 500 nm in a range between 1 and 99%.

The blocking element, in a particular embodiment is constituted by a multilayer substrate wherein at least one of said layers contains the blocking pigment of short wavelengths distributed over the surface of said layer.

In another embodiment, in the blocking element of short wavelengths, the substrate is a coating containing a pigment in the entire coating.

In another embodiment, the coating is one selected from gel, foam, emulsion, solution, dilution or a combination of the above.

In another aspect of the invention, the blocking method of short wavelengths in LED-type light sources is characterized in that it comprises the steps of: (i) selecting the mean optical density of a pigment, and (ii) pigmenting a substrate over its entire surface in such a way that the mean absorbance is between 1% and 99% in the range of short wavelengths between 380 nm and 500 nm.

The selection of the optical density is based on at least one of the following parameters: age of a user of LED-type light source, separation distance to the LED-type light source, size of the LED-type light source, exposure time to the light source by the user, ambient lighting of the place where the user interacts with the LED-type light source the type of device, the emission intensity, and the possible retinal and/or corneal disease state.

In a particular embodiment of the element or method, the pigment is evenly distributed over the surface of the substrate.

In another aspect of the invention, the LED display comprises the blocking element of short wavelengths according to the above description and/or obtained by a manufacturing process comprising a step of reducing the emission of short wavelengths between 380-500 nm of the LEDs contained in the display. That is, the LED display with the blocking element or default so that it contains the essential characteristics of said blocking element.

In another aspect of the invention, the computer-implemented method of blocking the short wavelengths in LED-type light sources characterized in that it comprises the steps of: (i) calculating the emissions of harmful short wavelengths between 380 and 500 nm; and (ii) selectively reducing the emission of short wavelengths between 380-500 nm of the LEDs contained in at least a part of the display, based on the calculation set out in the previous step.

The modification on the display can be total (in the entire display) or in a part, since on certain occasions it may be necessary to maintain the pure color in certain parts, e.g. in design graphic applications or similar.

As in the previous case, the calculation of the harmful emissions is a function of at least one of the following variables: age of a user of LED-type light source, separation distance to the LED-type light source, size of the LED-type light source, exposure time to the light source by the user, ambient lighting of the place where the user interacts with the LED-type light source the type of device, the emission intensity and the possible retinal and/or corneal disease state.

In a particular embodiment, the computer-implemented method comprises a further step of detecting the background of an electronic document viewed by a user and a second step of switching said background to one with a reduced emission on the spectrum between 380-500 nm.

In another aspect of the invention, the portable electronic device comprises a LED display; one or more processors, a memory; and one or more programs wherein the program(s) are stored in the memory and configured to be executed by at least the processor(s), the programs including instructions for calculating the emissions of harmful short wavelengths between 380 and 500 nm; and selectively reducing the emission of short wavelengths between 380-500 nm of at least a part of the LEDs contained in the display.

As in the computer-implemented method, it is possible to reduce via software a part of the LEDs contained in the display.

The selective reduction is carried out by modifying the colors in the operating system in a practical embodiment of the device.

In another practical embodiment of the device, the selective reduction is temporarily progressive depending on the exposure time of the user and the time of day.

In one final aspect of the computer program product with instructions configured for execution by one or more processors that, when running, carry out the method according to the computer-implemented method.

In all aspects of the invention is equally achieve the protection of the retina, cornea and crystalline of the harmful action of the short wavelengths, as well as eliminate the eyestrain, improve the comfort and visual function, final objects of the invention, since this damage in eye not properly protected is a cumulative and irreversible damage.

Throughout the description and claims, the word 'comprises' and its variations are not intended to exclude other technical features, additives, components or steps. For those skilled in the art, other objects, advantages and characteristics of the invention will emerge in part from the description and in part from the practice of the invention. The following examples and drawings are provided by way of illustration and are not intended to be limiting of the present invention. Furthermore, the present invention covers all the possible combinations of particular and preferred embodiments herein indicated.

BRIEF DESCRIPTION OF THE DRAWINGS

Described very briefly hereinafter are a series of drawings that help to better understand the invention, and which are expressly related to an embodiment of said invention that is presented as a non-limiting example thereof.

DETAILED DESCRIPTION OF THE INVENTION AND EXAMPLE

In the state of the art the degree of toxicity of the short wavelengths, produced by LED light of different spectral composition, due to the use of an electronic device equipped with this type of displays (LED) on retinal pigment epithelial cells, has not been described.

Figure 4:
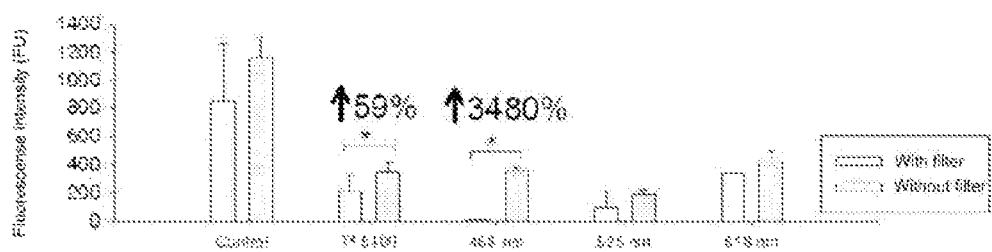
FIG. 4 shows a graph with the LED light effect and the photoprotective effect of a blocking element that selectively absorbs the short wavelengths on the cell viability, indicative of cell survival in human retinal pigment epithelial cells.

The specific objectives of the toxicity test and the provided solution are as follows:

Study the cell viability of the retinal tissue in vitro after exposure to different LEDs that emit radiation of different spectral composition, as shown in FIG. 4.

Figure 5:
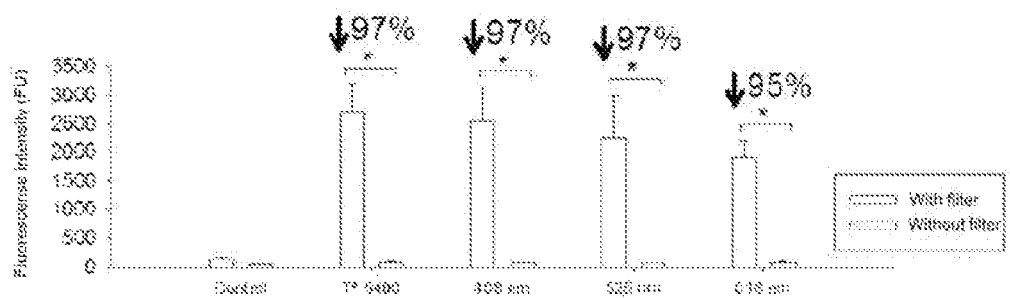
FIG. 5 shows the LED light effect and the photoprotective effect of a blocking element that selectively absorbs the short wavelengths on the activation of the human histone H2AX, indicative of DNA damage in human retinal pigment epithelial cells.

Assess the DNA damage of the retinal tissue in vitro after exposure to different LEDs that emit radiation of different spectral composition, as shown in FIG. 5.

Figure 6:
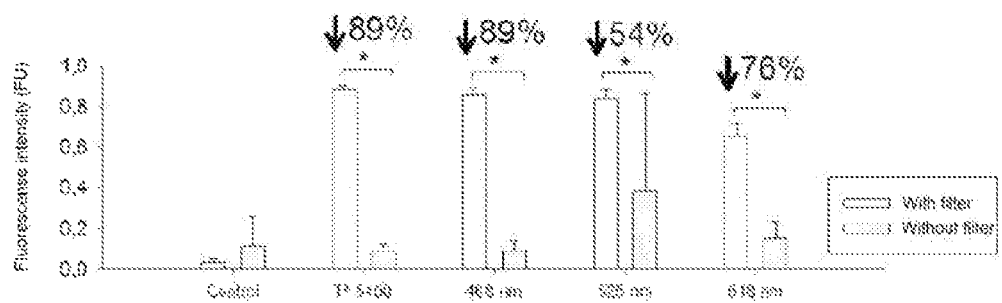
FIG. 6 shows the LED light effect and photoprotective effect of a blocking element that selectively absorbs the short wavelengths on the activation of the caspase-3, -7, indicative of apoptosis in human retinal pigment epithelial cells.

Determine the apoptosis of the retinal tissue in vitro after exposure to different LEDs that emit radiation of different spectral composition, as shown in FIG. 6.

Following the assessment and determination of toxicity, the solutions proposed in the present invention are assessed.

TABLE 1

| Reagent/Equipment and Catalogue and lot Numbers | Supplier |
| --- | --- |
| Human Retinal Pigment Epithelial cell #P10873- | Sciencell |
| Poly-L-lysine # P4707 Lot No BCBC0503 | Sigma Aldrich |
| Epithelial cell medium #960106 | Sciencell |
| TMRM #668 | Invitrogen |
| CM-H2DCFDA #C6827 | Invitrogen |
| Rabbit anti caspase3 antibody #9661 Lot No P42574 | Cell Signalling |
| Mouse anti H2AX antibody #ab22551 Lot No 820115 | Abcam |
| Goat anti-rabbit antibody Alexa 594 #A11012 Lot No 695244 | Invitrogen |
| Goat anti-mouse antibody Alexa 633 #A21050 Lot No 690316 | Invitrogen |
| 96well, black clear Imaging Plate #353219 | Becton Dickinson |
| Bovine serum albumin #A2153 | Sigma |
| Paraformaldehyde #16005 | Sigma |
| BD Pathway 855 | Becton Dickinson |
| Hydrogen Peroxide Sol. 3%. Lot D401A | |

Figure 2A:
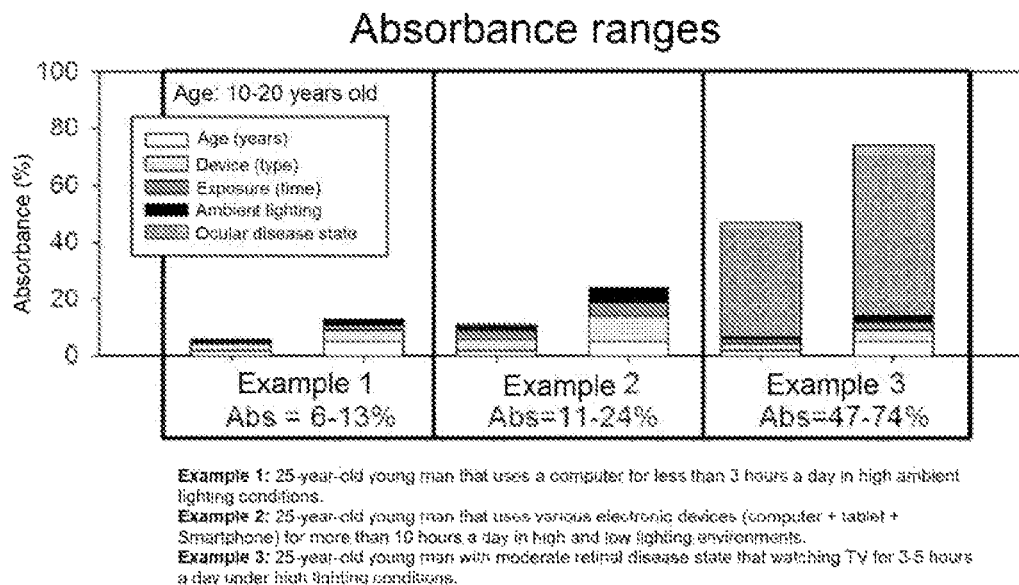
FIG. 2 shows the selective absorbance of the blocking element of short wavelengths of the present invention for three examples of people of different age: 25 years old (FIG. 2a), 45 years old (FIG. 2b) and 76 years old (FIG. 2c).

In table 1, a summary of the reagents, equipment and supplied material used in the study is found. On the other hand, a lighting device has been designed comprising five differentiated lighting zones separated off from each other by discriminating barriers of a white material. Each one of the zones contains a LED producing light of irradiance 5 mW/cm$^2$ but emitting light with different spectral composition:

Blue LED (468 nm)
Green LED (525 nm)
Red LED (616 nm)
White LED; Color T°=5400° K In FIG. 2A, Example 1 is a 25-year old person that uses a computer for less than three hours a day in high ambient high conditions, Example 2 is a 25-year old person that uses various electronic devices (computer+table+smartphone) for more than 10 hours a day in low and high lighting environments, and Example 3 is a 25-year old person that has a moderate retinal disease state and watches TV for three to five hours a day under high lighting conditions.

Figure 2B:
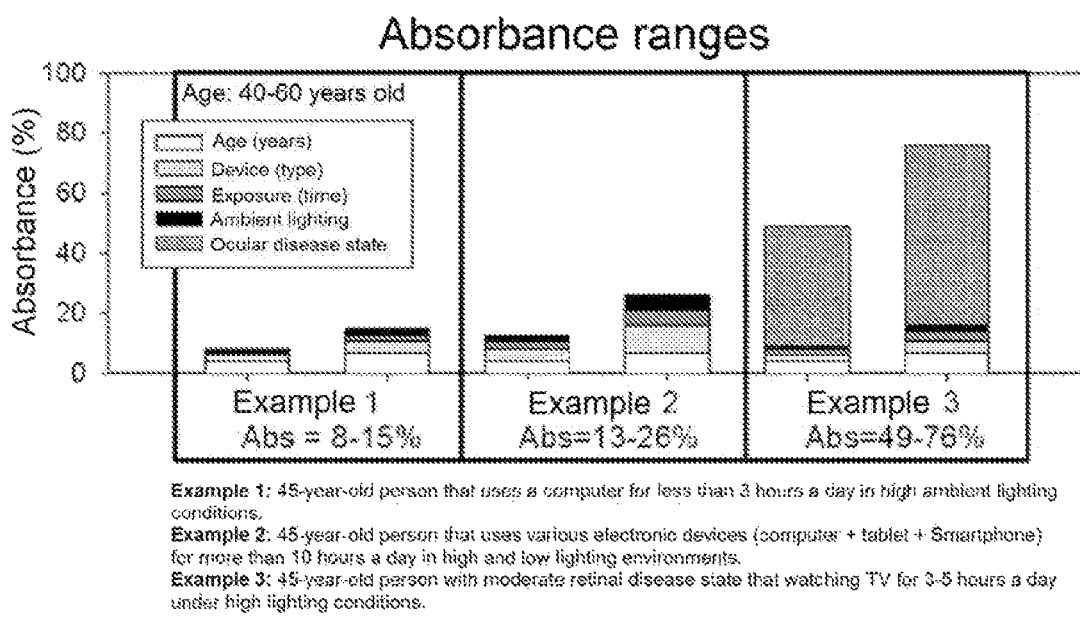

In FIG. 2B, Example 1 is a 45-year old person that uses a computer for less than three hours a day in high ambient high conditions, Example 2 is a 45-year old person that uses various electronic devices (computer+table+smartphone) for more than 10 hours a day in low and high lighting environments, and Example 3 is a 45-year old person that has a moderate retinal disease state and watches TV for three to five hours a day under high lighting conditions.

Figure 2C:
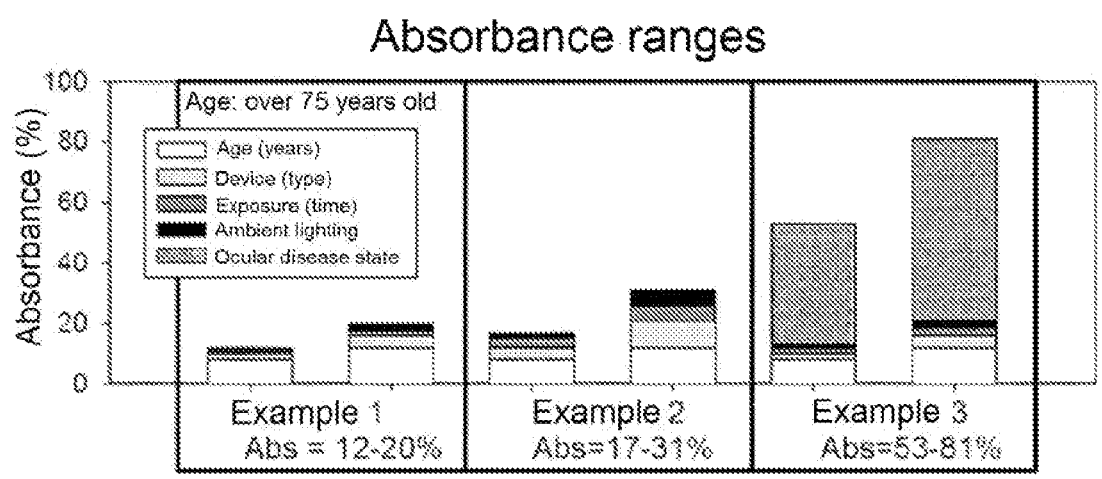

In FIG. 2C, Example 1 is a 76-year old person that uses a computer for less than three hours a day in high ambient high conditions, Example 2 is a 76-year old person that uses various electronic devices (computer+table+smartphone) for more than 10 hours a day in low and high lighting environments, and Example 3 is a 76-year old person that has a moderate retinal disease state and watches TV for three to five hours a day under high lighting conditions.

Figure 3:
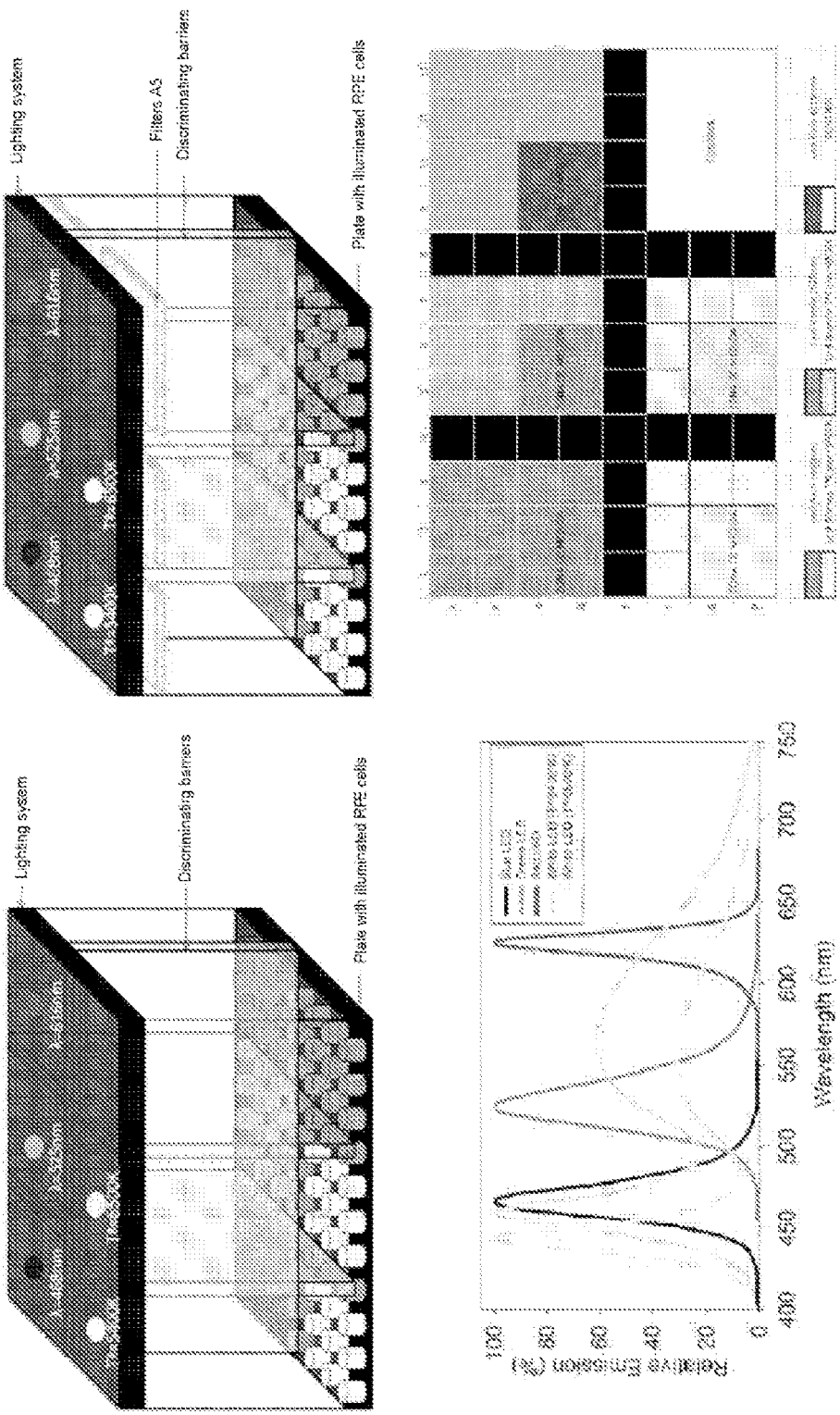
FIG. 3 shows a view of the LED-type light source used for the example that illustrates the present invention. A. Schematic representation of the lighting device without and with the blocking element of short wavelengths used. B. Spectral emission curves of each of the used LEDs. C. Design of the well plate where the cells were seeded.

FIG. 3 represents schematically the lighting device used and the spectral emission curves of each of the LEDs. This device was placed on the culture plate, and the cells were exposed to LED light for 3 light-dark cycles (12 hours/12 hours) with and without the interposition of the blocking element of short wavelengths. As shown, there is a zone not illuminated by LEDs where the cells not exposed to light which were used as negative control are placed.

In this non-limitative, particular embodiment, the blocking element is defined as a blocking element of short wavelengths consisting of a substrate with a yellow pigment evenly distributed on its surface and, in that said pigment has an optical density such that it allows the selective absorption of short wavelengths between 380 nm and 500 nm in a range between 1 and 99%. More specifically, it is a film or multilayer film, where one of them is pigmented.

Cell Culture and Plate Design

The retinal pigment epithelial cells (RPE) were thawed following the supplier's instructions, in 'Epithelial cell culture medium', supplemented with fetal bovine serum (FBS) and growth factors. At 72 hours and once the culture reaches the confluence, the cells were raised with trypsin-EDTA and were seeded at a density of 5000 cells/well in a 96-well plate previously treated with poly-lysine. The culture was kept for 24 hours after which the medium was replaced by fresh medium (300 µl/well). This procedure was repeated each of the days in which the experiment was carried out to avoid evaporations by the heat produced by the lamps. The plate with the lighting device was placed within the incubator at 37° C. in an atmosphere of 5% $CO_2$.

The toxicity experiment was conducted after the cells were incubated in the presence of light of different spectral characteristics for 3 exposure/rest cycles of 12 hours per cycle.

The samples were washed with PBS and fixed with 4% paraformaldehyde for 15 minutes. After fixation, the cells were permeated with 0.3% Triton for 10 minutes. Once the samples were permeated, they were blocked with 5% BSA and the anti-caspase and anti-H2AX antibodies dissolved in 2.5% PBS+BSA were then added at a concentration of 1:400 for the determination of apoptosis and DNA damage respectively.

After an hour of incubation, the samples were washed with PBS, and secondary antibodies, Alexa 594 and Alexa 633, were added at the same concentration as the primary antibody and incubated for 30 minutes. After incubation, the samples were washed and the signal was read in the BD Pathway 855 fluorescence microscope. For the activation of caspases, images were captured at 633 nm of emission and for H2AX at 594 nm.

Statistical Analysis

Each experiment was repeated at least twice. The values are given as mean±standard deviation. The data were analyzed by statistical unpaired Student's t-test using the statistical software Statgraphics version Centurion XVI.I (USA). P-values of less than 0.05 were considered to be significant.

Results. Cell Viability

After a period of 3 light exposure cycles to for 12 hours, alternating with 3 recovery cycles for a further 12 hours, the nuclei of the primary human retinal pigment epithelial cells were DAPI-stained to count the number of cells per well.

The non-irradiated cells grew well in the wells, but irradiation with monochromatic LED light inhibited cell growth. Blue light (468 nm) produced a very significant reduction in the number of cells, although there was also an observable phototoxic effect for green light (525 nm). In the case of white light (T°=5400° K) no statistically significant differences were observed.

With the presence of the blocking element of short wavelengths, an increase of cell viability was observed, mainly in cells exposed to white light (T°=5400° K) and light blue (468 nm) as shown in the table 2.

TABLE 2

| Cell viability | Control | white LED (T ° = 5400° K) | Blue LED (468 nm) | Green LED (525 nm) | Red LED (616 nm) |
| --- | --- | --- | --- | --- | --- |
| Without blocking element (FU) | 855 ± 403 | 217 ± 108 | 10 ± 2 | 99 ± 114 | 339 ± 1 |
| With blocking element (FU) | 1156 ± 156 | 346 ± 71 | 358 ± 20 | 188 ± 43 | 420 ± 69 |
| p-value | — | 0.212 | 0.047* | 0.000* | 0.102 | 0.096 |
| Increase (%) | — | — | 59 | 3480 | — | — |

In FIG. 4, the LED light effect and the photoprotective effect of a blocking element that selectively absorbs the short wavelengths on the cell viability in human retinal pigment epithelial cells can be seen. FU means fluorescence unit.

Results: DNA Damage

To examine whether the radiation had some effect on the integrity of cellular DNA, cells were marked using H2AX antibody.

H2AX is a variant of the histone H2A that is involved in DNA repair, i.e. when there is damage in nuclear DNA. When the double-stranded DNA break occurs, H2AX histone is rapidly phosphorylated on serine 139 by kinase ATM and becomes Gamma-H2AFX.

This phosphorylation step can extend to several thousands of nucleosomes from the site of the double-strand break and can mark the surrounding chromatin in the recruitment of the proteins necessary for damage signaling and DNA repair. As part of post-translational modifications of apoptosis, caused by severe DNA damage, a high expression of phosphorylated H2AX is considered as an accurate indicator of apoptosis.

The results of experiments showed that anti-H2AX antibody recognizes sites of phosphorylated histones after irradiation with LED light indicating an activation of DNA repair mechanisms.

By interposing the blocking element of the short wavelengths, a significant decrease in activation of histone H2AX, indicative of less DNA damage, was observed. This decrease was 97% for white (T°=5400° K), blue (468 nm), and green (525 nm) LED light, and 95% in cells exposed to red LED light, as seen in table 3.

TABLE 3

| Activation of H2AX | Control | White LED (T ° = 5400° K) | Blue LED (468 nm) | Green LED (525 nm) | Red LED (616 nm) |
|---|---|---|---|---|---|
| Without blocking element (FU) | 131 ± 41 | 2697 ± 493 | 2537 ± 589 | 2258 ± 738 | 1920 ± 286 |
| With blocking element (FU) | 47 ± 1 | 83 ± 20 | 76 ± 7 | 63 ± 10 | 91 ± 15 |
| p-value | 0.024* | 0.000* | 0.002* | 0.001* | 0.000* |
| Decrease (%) | — | 97% | 97% | 97% | 95% |

In FIG. 5, the LED light effect and the photoprotective effect of a blocking element that selectively absorbs the short wavelengths on the activation of histone H2AX in human retinal pigment epithelial cells, is shown. FU means fluorescence unit.

Results: Apoptosis

The activation of caspase-3 and -7 was determined, since these enzymes are involved in the regulation and execution of apoptosis. The cells were marked using the anti-caspase antibody.

Irradiation with LED light in the cells caused an increase in the percentage of apoptotic cells in the culture. The caspase activation is observed as a pinkish color around the blue-stained nucleus (DAPI).

The interposition of the blocking element of short wavelengths induced a significant decrease in caspase activation, indicative of apoptosis in cells exposed to the different LED light sources. This decrease was 89% for white (T°=5400° K) and blue (468 nm) lights, 54% for green light (525 nm), and 76% for red light, as shown in table 4.

TABLE 4

| Activation of caspases | Control | White LED (T ° = 5400° K) | Blue LED (468 nm) | Green LED (525 nm) | Red LED (616 nm) |
|---|---|---|---|---|---|
| Without blocking element (FU) | 0.037 ± 0.02 | 0.888 ± 0.02 | 0.861 ± 0.03 | 0.839 ± 0.05 | 0.655 ± 0.07 |
| With blocking element (FU) | 0.114 ± 0.15 | 0.094 ± 0.03 | 0.094 ± 0.05 | 0.386 ± 0.48 | 0.155 ± 0.08 |
| p-value | 0.541 | 0.000* | 0.000* | 0.312 | 0.006* |
| Reduction (%) | — | 89% | 89% | 54% | 76% |

In FIG. 6, the LED light effect and photoprotective effect of a blocking element that selectively absorbs the short wavelengths on the activation of the caspase-3, -7 in human retinal pigment epithelial cells, is shown. FU means fluorescence unit.

Following an analysis of the problem and an example of solution, the light, especially that of smaller wavelengths, in 3 cycles of 12 hours of exposure alternating with 12 hours of recovery, affects the growth of the human retinal pigment epithelial cells. An increase in the number of cells expressing the histone H2AX (DNA damage) y caspase-3 and -7 (apoptosis) occurs.

In all cases the blocking element that selectively absorbs the short wavelengths exerts a protective effect against the damaging effects of light on the human retinal pigment epithelial cells.

Selection of the Optical Density of Blocking Element that Absorbs the Short Wavelengths It is obvious for a person skilled in the art that other particular embodiments can be possible, and not only that shown in the previous example. However, all particular realizations have to take into account that the absorbance that blocks the wavelengths between 380 and 500 nm must be selected, as well as reduced, via software, said emission selectively without reducing the intensity or amount of light.

For this reason, the present invention establishes a series of factors (table 5) to which are endowed them a certain maximum and minimum weight to precisely set the maximum and minimum absorbance for each individual:

TABLE 5

| Factor | Degree | Maximum limit (%) | Minimum limit (%) |
|---|---|---|---|
| Age (years) | 0-10 | 4 | 1 |
| | 10-20 | 5 | 2 |
| | 20-40 | 5 | 2 |
| | 40-60 | 7 | 4 |
| | 60-75 | 10 | 8 |
| | >75 | 12 | 8 |

TABLE 5-continued

| Factor | Degree | Maximum limit (%) | Minimum limit (%) |
|---|---|---|---|
| Type of used devices (working distance) | Smartphones (25-40 cm) | 2 | 1 |
| | Tablets (25-40 cm) | 3 | 1 |
| | Computer screens (41-70 cm) | 4 | 2 |
| | Television screens (>70 cm) | 4 | 2 |
| Total exposure time (hours) | <3 | 2 | 1 |
| | 3-5 | 3 | 2 |
| | 5-8 | 4 | 3 |
| | 8-10 | 5 | 3 |
| | >10 | 5 | 3 |
| Conditions of lowest ambient lighting during the use of the devices (cd/m$^2$) | Photopic (>5) | 2 | 1 |
| | Mesopic (0.005-5) | 5 | 2 |
| | Scotopic (<0.005) | 10 | 4 |
| Disease State | Retinal disease states | | |
| | Mild stage | 50 | 30 |
| | Moderate stage | 60 | 40 |
| | Severe stage | 70 | 50 |
| | Corneal disease states | | |
| | Mild stage | 20 | 10 |
| | Moderate stage | 30 | 20 |
| | Severe stage | 40 | 30 |
| | Palpebral disease states | 5 | 2 |
| | Conjunctival disease states | 5 | 2 |
| | Scleral disease states | 5 | 2 |
| | Glaucoma | 20 | 10 |
| | Pseudophakic/Aphakia | 30 | 10 |

The sum of the various factors listed by way of example in table 5 is what gives as a result a maximum and minimum absorbance threshold corresponding to FIG. 2, where, by way of an example, for a user between 25 years old (max. 5, min 2) that works with a computer (4/2), with an exposure time to the light source by the user less than 3 hours (2/1), with an ambient lighting of the place where the user interacts with the photopic LED-type light source (2/1) and without disease states, is stated that we would have a maximum absorbance in the range of 380-500 nm of (5+2+2+2) of 13%, while the minimum of absorbance would be 6%, as shown, for example in FIG. 2. However, if the same individual uses various electronic devices (computer, tablet and smartphone) for more than 10 hours in environments of high and low lighting, the preferred absorbance range would be between 11-24%. On the other hand, if the individual has a moderate retinal disease state and was exposed to television for 3-5 hours a day in high light conditions, the recommended absorbance range would be 47-74%.

Some might think it is not necessary to have a maximum absorbance range and completely block the passage of the short wavelengths between 380-500. However, the total blocking of the blue light produces effects both on the visibility of the screen and on the individual's circadian cycle itself, so it is logical to set a minimum and maximum absorbance range, minimizing such negative effects.

Examples and practical embodiments to achieve this selective absorbance vary since it can be a multilayer substrate (the blocking element used in the example), a coating (gel, foam, emulsion, solution, dilution or mixture) with a pigment of this optical density, or reduction via software of the emission on the spectrum of 380-500 nm.

Figure 1:
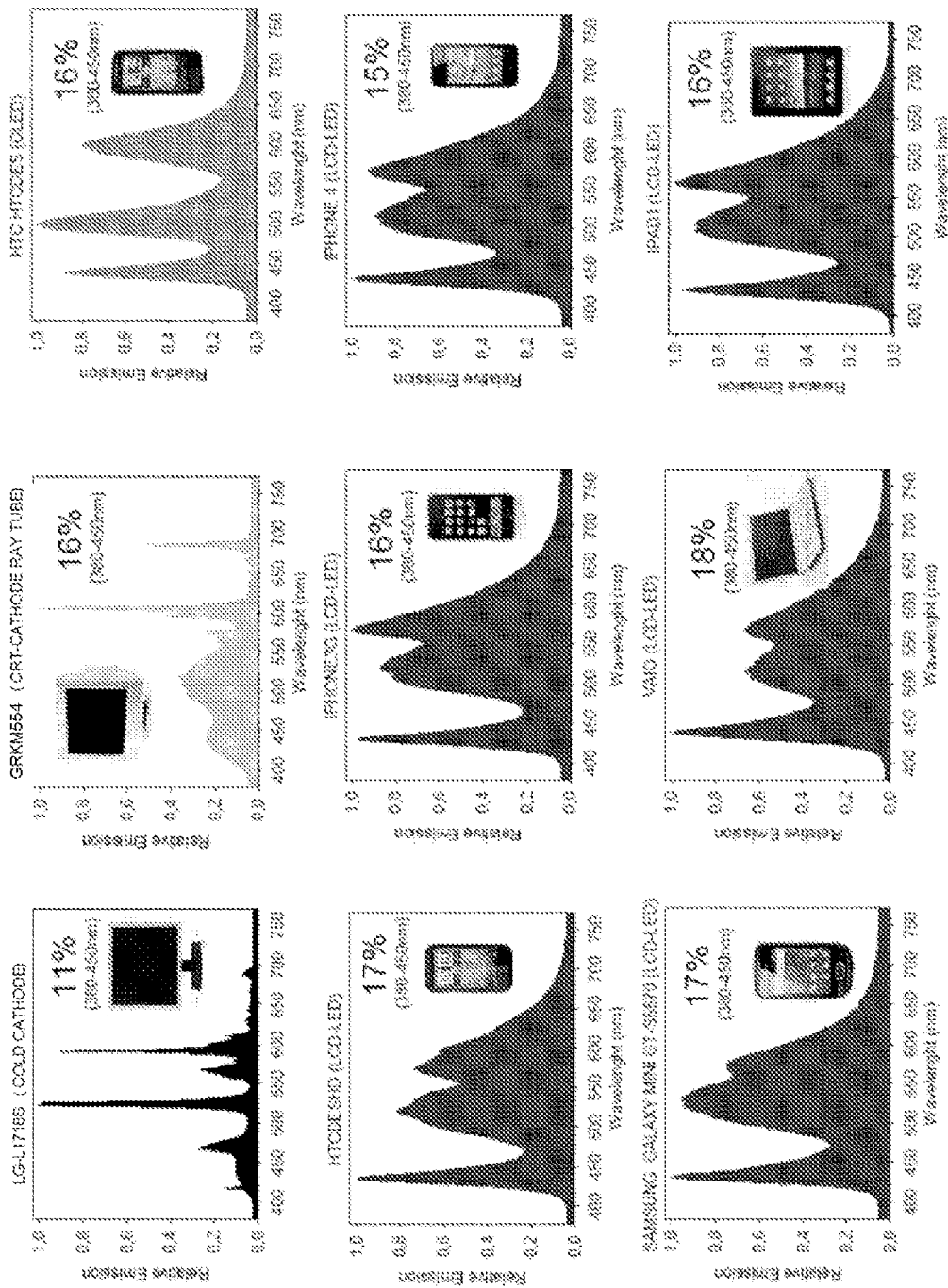
FIG. 1 shows different graphs of emissions for commercial electronic products with LED-type display.
Figure 7:
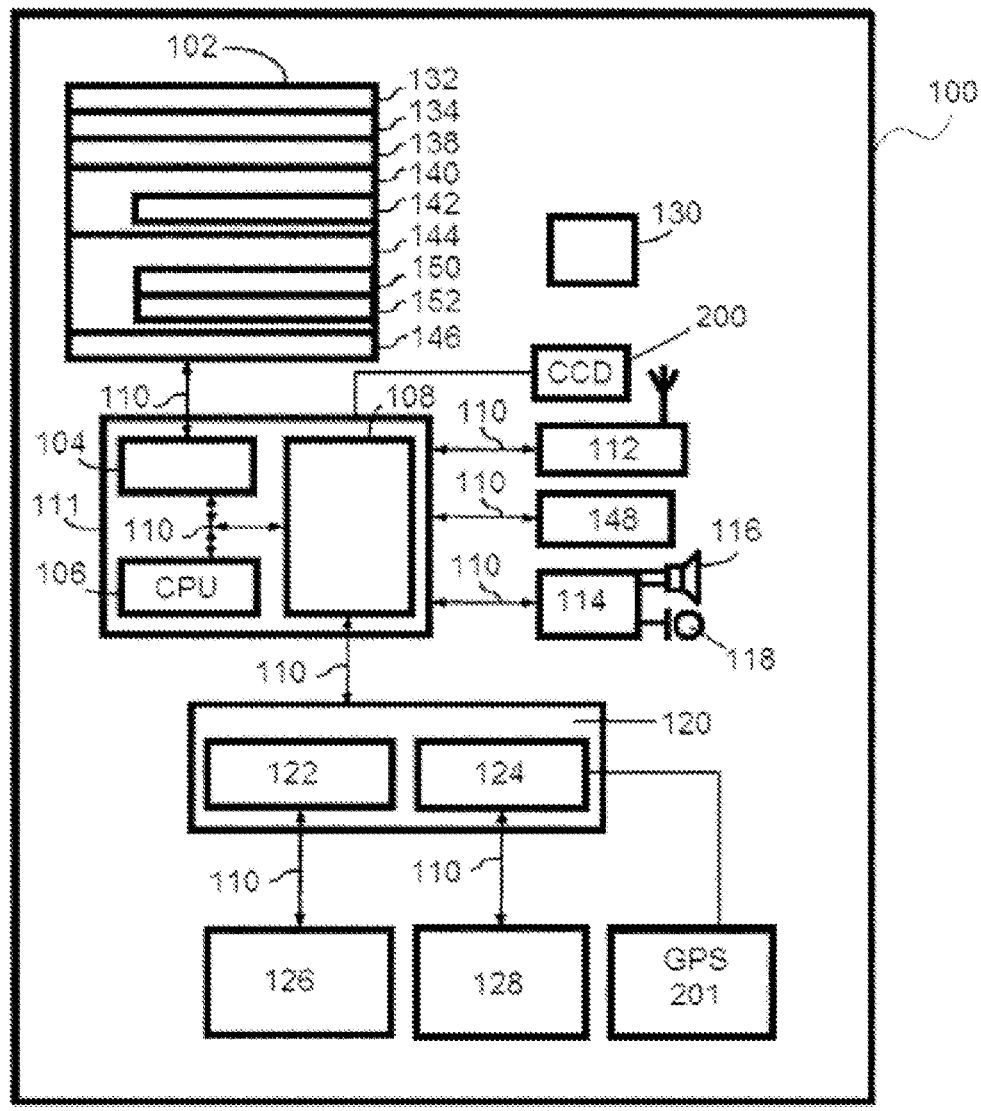
FIG. 7 shows a schema of a portable electronic device as that used in the present invention.

The portable electronic device (100) as one that can be used in the present invention according to some practical embodiments is shown in FIG. 7. More specifically, the portable electronic device 100 of the invention includes a memory 102, a memory controller 104, one or more processing units (CPU) 106, a peripherals interface 108, a RF circuitry 112, an audio circuitry 114, a speaker 116, a microphone 118, an input/output (I/O) subsystem 120, a LED display 126, other input or control devices 128, and an external port 148. These components communicate over the one or more communication buses or signal lines 110. The device 100 can be any portable electronic device, including but not limited to a handheld computer, a tablet computer, a mobile phone, a media player, a personal digital assistant (PDA), or the like, including a combination of two or more of these items. It should be appreciated that the device 100 is only one example of a portable electronic device 100, and that the device 100 may have more or fewer components than shown, or a different configuration of components. The various components shown in FIG. 1 may be implemented in hardware, software or a combination of both hardware and software, including one or more signal processing and/or application specific integrated circuits. In the same way, the LED display 126 has been defined, although the invention may also be implemented in devices with a standard display.

The memory 102 may include high-speed random-access memory and may also include non-volatile memory, such as one or more magnetic disk storage devices, flash memory devices, or other non-volatile solid state memory devices. In some embodiments, the memory 102 may further include storage remotely located from the one or more processors 106, for instance network attached storage accessed via the RF circuitry 112 or external port 148 and a communications network (not shown) such as the Internet, intranet(s), Local Area Networks (LANs), Wide Local Area Networks (WLANs), Storage Area Networks (SANs) and the like, or any suitable combination thereof. Access to the memory 102 by other components of the device 100, such as the CPU 106 and the peripherals interface 108, may be controlled by the memory controller 104.

The peripherals interface 108 couples the input and output peripherals of the device to the CPU 106 and the memory 102. The one or more processors 106 run various software programs and/or sets of instructions stored in the memory 102 to perform various functions for the device 100 and to process data.

In some embodiments, the peripherals interface 108, the CPU 106, and the memory controller 104 may be implemented on a single chip, such as a chip 111. In some other embodiments, they may be implemented on separate chips.

The RF (radio frequency) circuitry 112 receives and sends electromagnetic waves. The RF circuitry 112 converts electrical signals to/from electromagnetic waves and communicates with communications networks and other communications devices via the electromagnetic waves. The RF circuitry 112 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 112 may communicate with the networks, such as the Internet, also referred to as the World Wide Web (WWW), an Intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS), or any other suitable communication protocol, including communication protocols not yet developed as of the filing date of this document.

The audio circuitry 114, the speaker 116, and the microphone 118 provide an audio interface between a user and the device 100. The audio circuitry 114 receives audio data from the peripherals interface 108, converts the audio data to an electrical signal, and transmits the electrical signal to the speaker 116. The speaker converts the electrical signal to human-audible sound waves. The audio circuitry 114 also receives electrical signals converted by the microphone 116 from sound waves. The audio circuitry 114 converts the electrical signal to audio data and transmits the audio data to the peripherals interface 108 for processing. Audio data may be may be retrieved from and/or transmitted to the memory 102 and/or the RF circuitry 112 by the peripherals interface 108. In some embodiments, the audio circuitry 114 also includes a headset jack (not shown). The headset jack provides an interface between the audio circuitry 114 and removable audio input/output peripherals, such as output-only headphones or a headset with both output (headphone for one or both ears) and input (microphone).

The I/O subsystem 120 provides the interface between input/output peripherals on the device 100, such as the LED display 126 and other input/control devices 128, and the peripherals interface 108. The I/O subsystem 120 includes a LED-display controller 122 and one or more input controllers 124 for other input or control devices. The one or more input controllers 124 receive/send electrical signals from/to other input or control devices 128. The other input/control devices 128 may include physical buttons (e.g., push buttons, rocker buttons, etc.), dials, slider switches, and/or geographical location means 201, such as GPS or similar.

In this practical embodiment, the LED display 126 provides both an output interface and an input interface between the device and a user. The LED-display controller 122 receives/sends electrical signals from/to the LED display 126. The LED display 126 displays visual output to the user. The visual output may include text, graphics, video, and any combination thereof. Some or all of the visual output may correspond to user-interface objects, further details of which are described below.

The LED display 126 also accepts input from the user based on haptic contact. The LED display 126 forms a touch-sensitive surface that accepts user input. The LED display 126 and the LED-display controller 122 (along with any associated modules and/or sets of instructions in the memory 102) detects contact (and any movement or break of the contact) on the LED display 126 and converts the detected contact into interaction with user-interface objects, such as one or more soft keys, that are displayed on the LED display. In an exemplary embodiment, a point of contact between the LED display 126 and the user corresponds to one or more digits of the user.

The LED display 126 is or may be formed by a plurality of light-emitter diodes, and more specifically formed by white LEDs, although other type of LED emitters may be used in other embodiments.

The LED display 126 and LED-display controller 122 may detect contact and any movement or break thereof using any of a plurality of touch sensitivity technologies, including but not limited to capacitive, resistive, infrared, and surface acoustic wave technologies, as well as other proximity sensor arrays or other elements for determining one or more points of contact with the LED display 126.

The device 100 also includes a power system 130 for powering the various components. The power system 130 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the software components include an operating system 132, a communication module (or set of instructions) 134, a contact/motion module (or set of instructions) 138, a graphics module (or set of instructions) 140, a user interface state module (or set of instructions) 144, and one or more applications (or set of instructions) 146.

The operating system 132 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 134 facilitates communication with other devices over one or more external ports 148 and also includes various software components for handling data received by the RF circuitry 112 and/or the external port 148. The external port 148 (e.g., Universal Serial Bus (USB), FIREWIRE, etc.) is adapted for coupling directly to other devices or indirectly over a network (e.g., the Internet, wireless LAN, etc.).

The contact/motion module 138 detects contact with the LED display 126, in conjunction with the LED-display controller 122. The contact/motion module 138 includes various software components for performing various operations related to detection of contact with the LED display 122, such as determining if contact has occurred, determining if there is movement of the contact and tracking the movement across the LED display, and determining if the contact has been broken (i.e., if the contact has ceased). Determining movement of the point of contact may include determining speed (magnitude), velocity (magnitude and direction), and/or an acceleration (including magnitude and/or direction) of the point of contact. In some embodiments, the contact/motion module 126 and the LED display controller 122 also detects contact on the LED pad.

The graphics module 140 includes various known software components for rendering and displaying graphics on the LED display 126. Note that the term "graphics" includes any object that can be displayed to a user, including without limitation text, web pages, icons (such as user-interface objects including soft keys), digital images, videos, animations and the like.

In some embodiments, the graphics module 140 includes an optical intensity module 142. The optical intensity module 142 controls the optical intensity of graphical objects, such as user-interface objects, displayed on the LED display 126. Controlling the optical intensity may include increasing or decreasing the optical intensity of a graphical object. In some embodiments, the increase or decrease may follow predefined functions.

The user interface state module 144 controls the user interface state of the device 100. The user interface state module 144 may include a lock module 150 and an unlock module 152. The lock module detects satisfaction of any of one or more conditions to transition the device 100 to a user-interface lock state and to transition the device 100 to the lock state. The unlock module detects satisfaction of any of one or more conditions to transition the device to a user-interface unlock state and to transition the device 100 to the unlock state.

The one or more applications 130 can include any applications installed on the device 100, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player (which plays back recorded music stored in one or more files, such as MP3 or AAC files), etc.

In some embodiments, the device 100 may include one or more optional optical sensors (not shown), such as CMOS or CCD image sensors, for use in imaging applications.

Thus, the portable electronic device (100) essentially comprises, a LED display (126); one or more processors (106); a memory (102); and one or more programs wherein the program(s) (132 to 146) are stored in the memory (102) and configured to be executed by at least the processor(s) (106), the programs (132 to 146) including instructions to calculate the emissions of harmful short wavelengths between 380 and 500 nm and selectively reducing the emission of short wavelengths between 380-500 nm of at least a portion of the LEDs contained in the display (126). All of this as has already been indicated above.

The selective reduction is carried out by modifying the colors in the operating system (134) or in the color intensity module (142). In any case, there is also the possibility that said selective reduction is temporarily progressive so that the greater exposure time to the screen (126) of device (100), the greater reduction will be.

Finally, the computer program product with instructions configured for execution by one or more processors (106) that, when executing by a portable electronic device (100) as describe, said device (100) carries out the method according to the computer-implemented method to block the short wavelengths in LED-type light sources characterized in that it comprises the steps of: (i) calculating the emissions of harmful short wavelengths between 380 and 500 nm; and (ii) selectively reducing the emission of short wavelengths between 380-500 nm of the LEDs contained in the display depending on the calculation set out in the step (i).

The calculation of the harmful emissions is a function of at least one of the following variables: age of a user of LED-type light source, separation distance to the LED-type light source, size of the LED-type light source, exposure time to the light source by the user, ambient lighting of the place where the user interacts with the LED-type light source and the possible retinal and/or corneal disease state.

This computer program product can be physically implemented in the display hardware itself or in the video controller of a computer system comprising a LED-type display.

The protection of the retina, cornea and crystalline of the harmful action of the short wavelengths, as well as the elimination of the eyestrain, the improvement of the comfort and visual function, and the avoidance of the insomnia, final objects of the invention, are also achieved both with the computer-implemented method and with the portable electronic device (100), and with the described computer product.

One of the possibilities given by the invention is the possibility of changing the background of any document to one less aggressive for the human eye. Indeed, today, most of the documents have a white background, while its content is typically in a color that offers a strong contrast, like black, blue, red or green. This is conditioned by the fact that electronic documents, in general, try to imitate the documents written on paper, in addition to minimize the cost of printing of said documents.

However, that contrast, as described, implies a strong light emission with a harmful content for the human eye. Therefore, and thanks to the described method, the computer-implemented method, the device, and the computer product implement a further step of detecting the background of the document shown to the user, and a second step of switching said background to one with a reduced emission on the spectrum indicated.

Test of Lighting Characterization of Portable Electronic Devices of the Type of Tablets with LED Backlit Displays.

In order to justify the convenience of the invention, a test of lighting characterization of several tablets in the market and LED-backlit has been implemented.

The following concepts are defined in the test:

Emission spectrum is the set of frequencies of the electromagnetic waves that are obtained by breaking down the radiation emitted by the light source.

Irradiance (mW/cm2): Radiometric magnitude used to describe the incident power per unit area of all types of electromagnetic radiation.

The aim of the test is to determine the lighting characteristics of 3 display of tablets with LED backlight which project different images on their display:
a) Determine the emission spectrum of the light sources
b) Determine the irradiance of the light sources
c) Calculate the irradiance for every wavelength from the measurement of the emission spectrum of the display and the total irradiance.

The measures were performed on the models Apple IPad 4, Asus Memo Pad Smart y Samsung Galaxy Tab 10.1 (all trademarks registered by their respective owners) for a total of 22 wallpapers of different colors. The 3 primary colors (red, green and blue) were used, to which variations of hue and saturation were performed. Likewise the measures were performed with a white background. The following table set out the hue, saturation and brightness of each of the colors of the image projected on the display of the tablets that have been assessed:

TABLE 6

|  | Hue | Saturation | Brightness | Red | Green | Blue |
| --- | --- | --- | --- | --- | --- | --- |
| Pure Red | 0 | 240 | 120 | 255 | 0 | 0 |
| Red 1 | 3 | 240 | 120 | 255 | 19 | 0 |
| Red 2 | 5 | 240 | 120 | 255 | 32 | 0 |
| Red 3 | 7 | 240 | 120 | 255 | 45 | 0 |
| Red A | 0 | 220 | 120 | 244 | 11 | 11 |
| Red B | 0 | 200 | 120 | 234 | 21 | 21 |
| Red C | 0 | 180 | 120 | 223 | 32 | 32 |
| Pure Green | 80 | 240 | 120 | 0 | 255 | 0 |
| Green 1 | 83 | 240 | 120 | 0 | 255 | 19 |
| Green 2 | 85 | 240 | 120 | 0 | 255 | 32 |
| Green 3 | 87 | 240 | 120 | 0 | 255 | 45 |
| Green A | 80 | 220 | 120 | 11 | 244 | 11 |
| Green B | 80 | 200 | 120 | 21 | 234 | 21 |
| Green C | 80 | 180 | 120 | 32 | 223 | 32 |
| Pure Blue | 160 | 240 | 120 | 0 | 0 | 255 |
| Blue 1 | 163 | 240 | 120 | 19 | 0 | 255 |
| Blue 2 | 165 | 240 | 120 | 32 | 0 | 255 |
| Blue 3 | 167 | 240 | 120 | 45 | 0 | 255 |

TABLE 6-continued

|  | Hue | Saturation | Brightness | Red | Green | Blue |
|---|---|---|---|---|---|---|
| Blue A | 160 | 220 | 120 | 11 | 11 | 244 |
| Blue B | 160 | 200 | 120 | 21 | 21 | 234 |
| Blue C | 160 | 180 | 120 | 32 | 32 | 223 |
| White | 160 | 0 | 240 | 255 | 255 | 255 |

To determine the emission spectrum of the LED light sources was used the Ocean Optics Redtide USB 650 spectrophotometer. The data were analyzed using the Ocean Optics SpectraSuite software and plotted using the Sigmaplot software.

The acquisition protocol used for acquisition of measurements was:

Exposure time: 200 milliseconds

No. of scans of intensity: 5 (Each measurement of intensity emission is obtained from an average of 5 measurements carried out by the instrument).

The total irradiance of the light sources was determined with a Thorlabs PM100USB radiometer at a distance of 35 cm.

For the calculation of irradiance according to its wavelength, the following mathematical analysis was carried out:

$$I(\lambda) = I_T \frac{E(\lambda)}{E_T}$$

Where:

$I(\lambda)$ is the irradiance depending on the wavelength.

$I_T$ is the total irradiance measured in the experimental procedure.

$E(\lambda)$ is the relative electromagnetic spectrum depending on the wavelength measured in the experimental procedure.

$E_T$ is the is the total electromagnetic spectrum measured in the experimental procedure.

Test Results for the Model Asus Memo Pad Smart

Figure 8A:
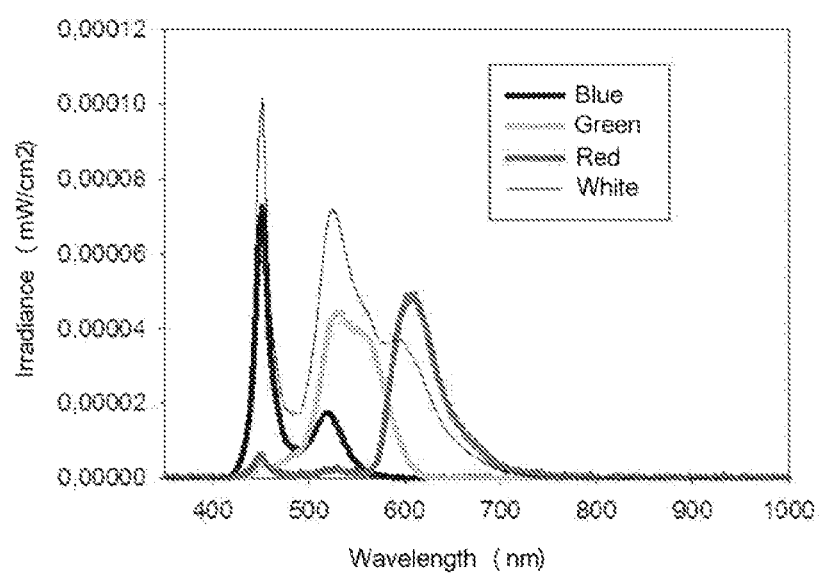
FIGS. 8A-8D show the graphs of results of the light characterization test for the model Asus Memo Pad Smart.
Figure 8B:
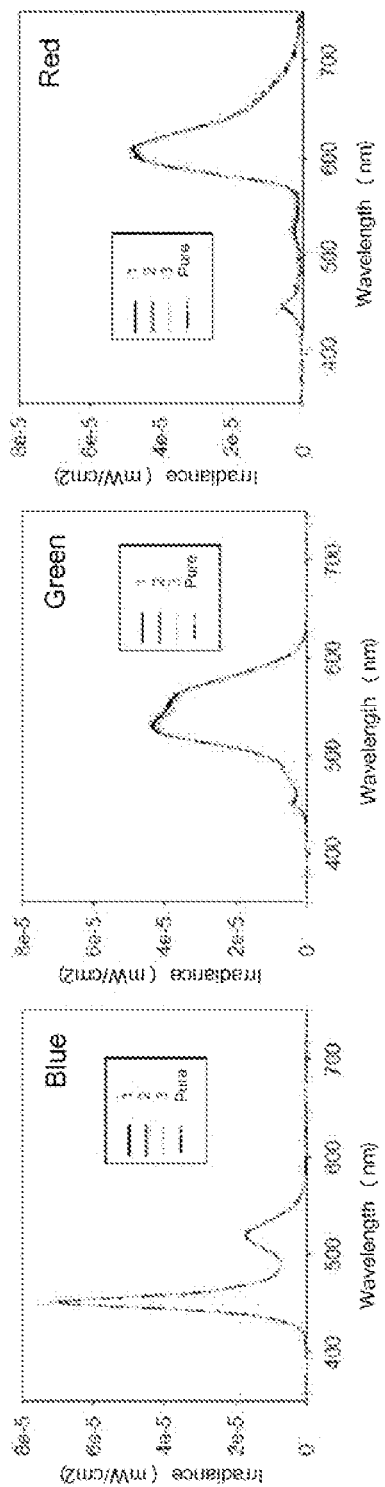
Figure 8C:
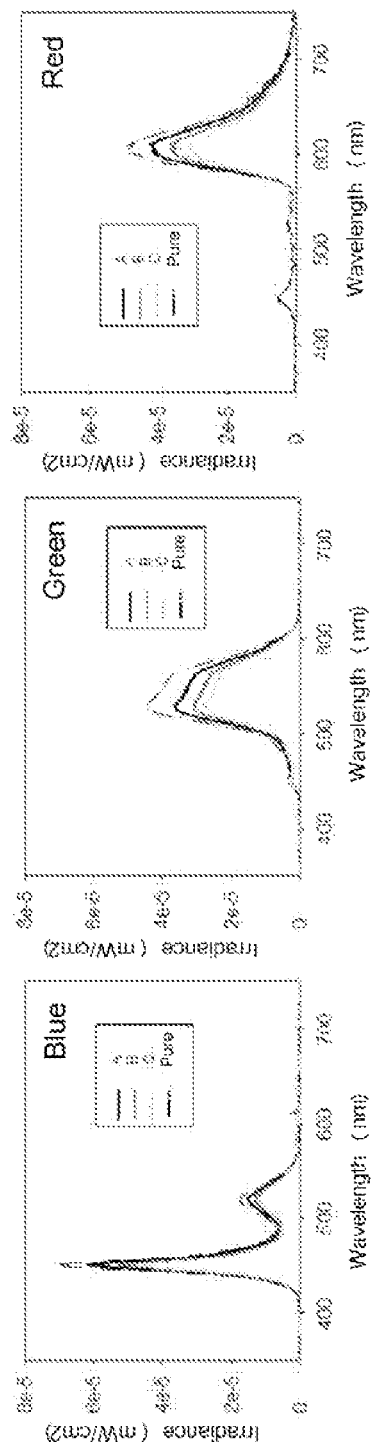

In the graph shown in FIG. 8A, the irradiance (mW/cm$^2$) depending on the wavelength of the tablet Asus Memo Pad Smart, using as a background the primary colors (red, green and blue) and a white image, is represented. In FIG. 8 and the subsequent graphs, the variation in lighting characteristics of the tablet display due to a change in the hue (FIG. 8B) or the saturation of the image of each of the primary colors (FIG. 8C) is represented.

Figure 8D:
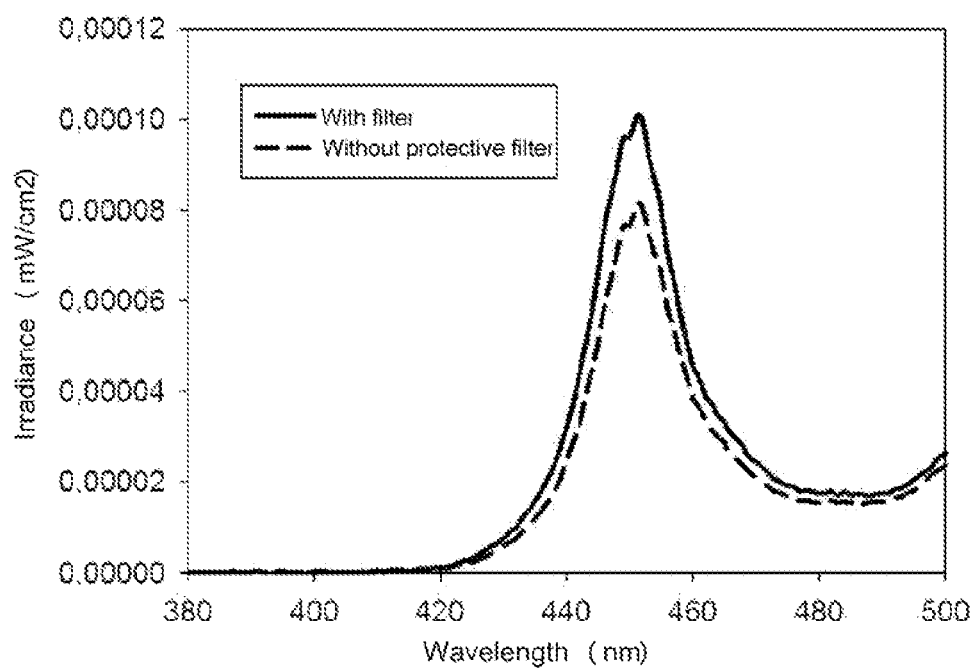

On the other hand in FIG. 8D, the irradiance (mW/cm$^2$) depending on the wavelength de la tablet Asus Memo Pad Smart with and without the interposition of a protective filter which partially absorbs the short wavelengths of the visible spectrum, according to the object of the invention, is represented. In table 7, the represented values are indicated:

TABLE 7

| wavelength (nm) | Absorption of the filter (%) |
|---|---|
| 410 | 18 |
| 415 | 24 |
| 420 | 28 |
| 425 | 23 |
| 430 | 23 |
| 435 | 24 |
| 440 | 23 |
| 445 | 24 |
| 450 | 20 |
| 455 | 17 |

TABLE 7-continued

| wavelength (nm) | Absorption of the filter (%) |
|---|---|
| 460 | 15 |
| 465 | 14 |
| 470 | 15 |
| 475 | 12 |
| 480 | 12 |
| 485 | 10 |
| 490 | 11 |
| 495 | 12 |
| 500 | 10 |

Test Results for the Model Apple iPad 4

In the graphs in FIG. 9, the irradiance (mW/cm$^2$) depending on the wavelength of the tablet iPad 4, using as a background the primary colors (red, green and blue) and a white image (FIG. 9A), is represented.

In the subsequent graphs, the variation in lighting characteristics of the tablet display due to a change in the hue (FIG. 9B) or the saturation of the image of each of the primary colors (FIG. 9C), is represented.

Figure 9A:
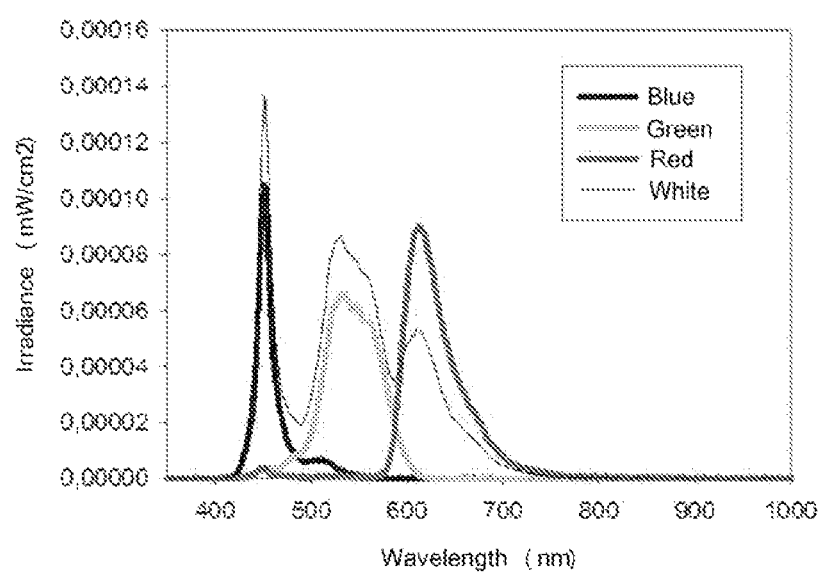
FIGS. 9A-9D show the graphs of results of the light characterization test for the model Apple iPad 4.
Figure 9B:
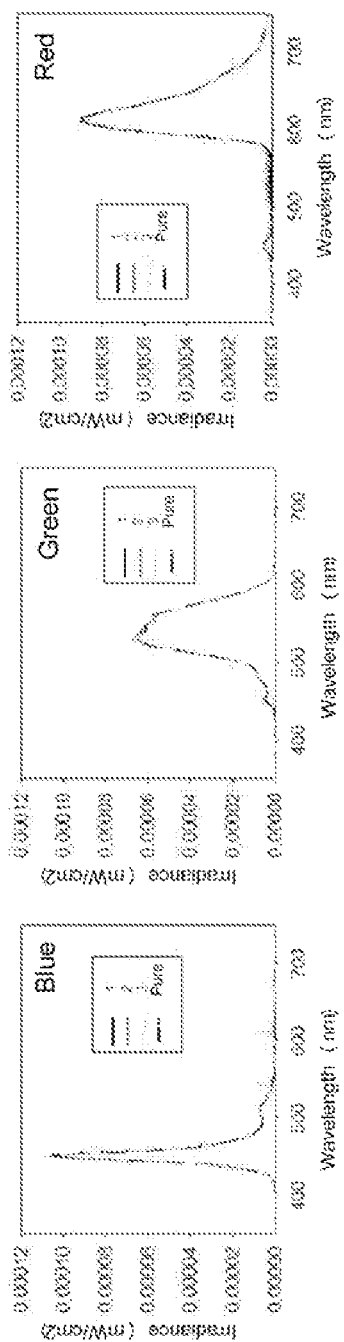
Figure 9C:
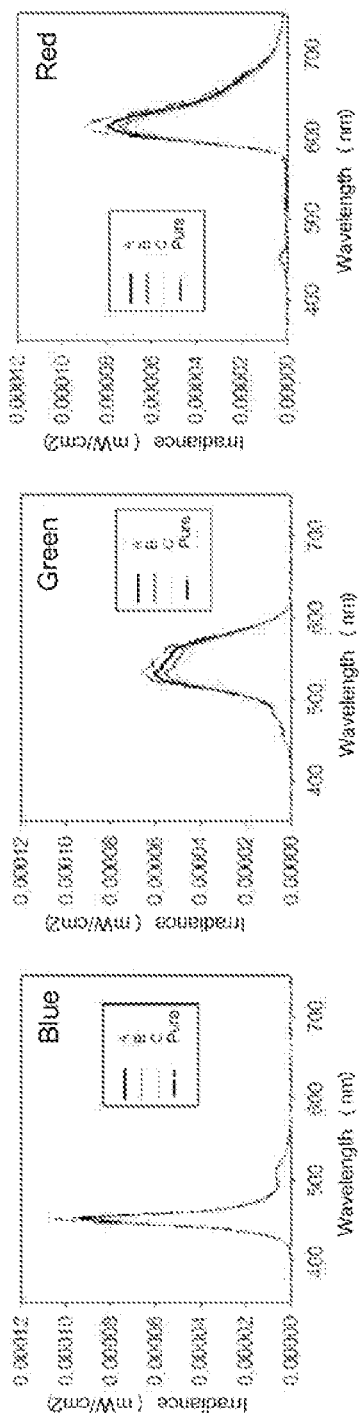
Figure 9D:
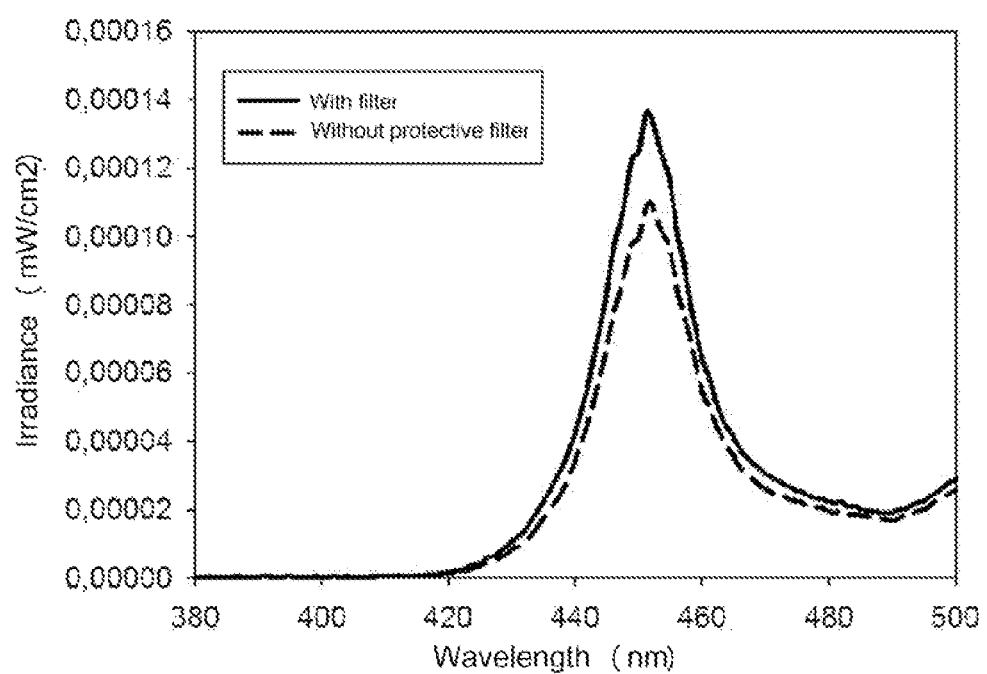

On the other hand in FIG. 9D, the irradiance (mW/cm$^2$) depending on the wavelength of the tablet iPad 4 with and without the interposition of a protective filter which partially absorbs the short wavelengths of the visible spectrum, according to the object of the invention, is represented. In table 8, the represented values are indicated:

TABLE 8

| wavelength (nm) | Absorption of the filter (%) |
|---|---|
| 410 | 22 |
| 415 | 14 |
| 420 | 15 |
| 425 | 21 |
| 430 | 22 |
| 435 | 22 |
| 440 | 19 |
| 445 | 20 |
| 450 | 20 |
| 455 | 17 |
| 460 | 15 |
| 465 | 13 |
| 470 | 14 |
| 475 | 12 |
| 480 | 13 |
| 485 | 9 |
| 490 | 11 |
| 495 | 11 |
| 500 | 11 |

Test Results for the Model Samsung Galaxy Tab 10.1

In the graphs in FIG. 10, the irradiance (mW/cm$^2$) depending on the wavelength of the tablet Samsung Galaxy Tab 10.1, using as a background the primary colors (red, green and blue) and a white image (FIG. 10A), is represented.

In the subsequent graphs, the variation in lighting characteristics of the tablet display due to a change in the hue (FIG. 10B) or the saturation of the image of each of the primary colors (FIG. 10C) is represented.

Figure 10A:
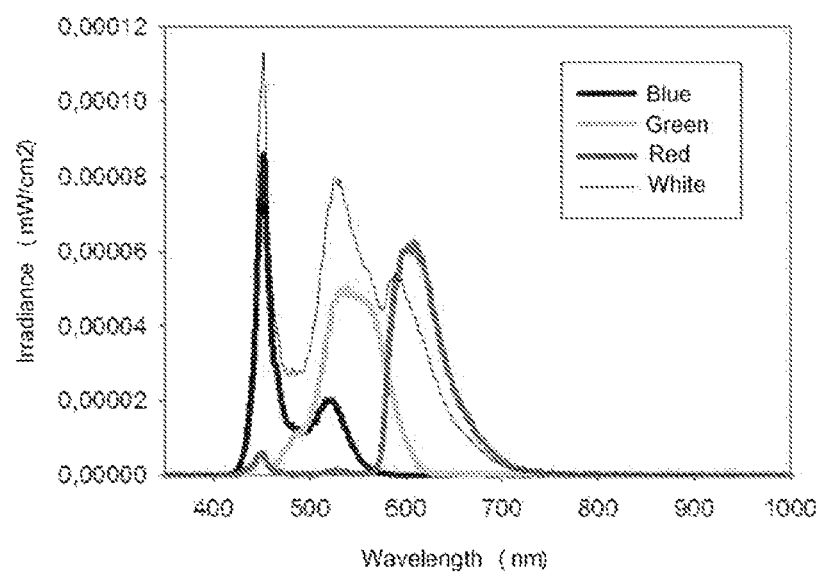
FIGS. 10A-10D show the graphs of results of the light characterization test for the model Samsung Galaxy Tab 10.1.
Figure 10B:
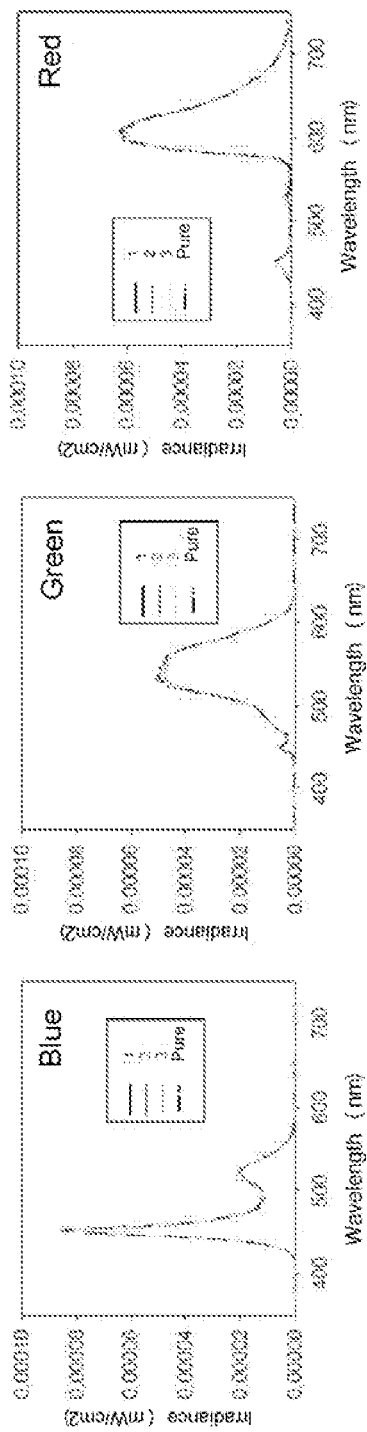
Figure 10C:
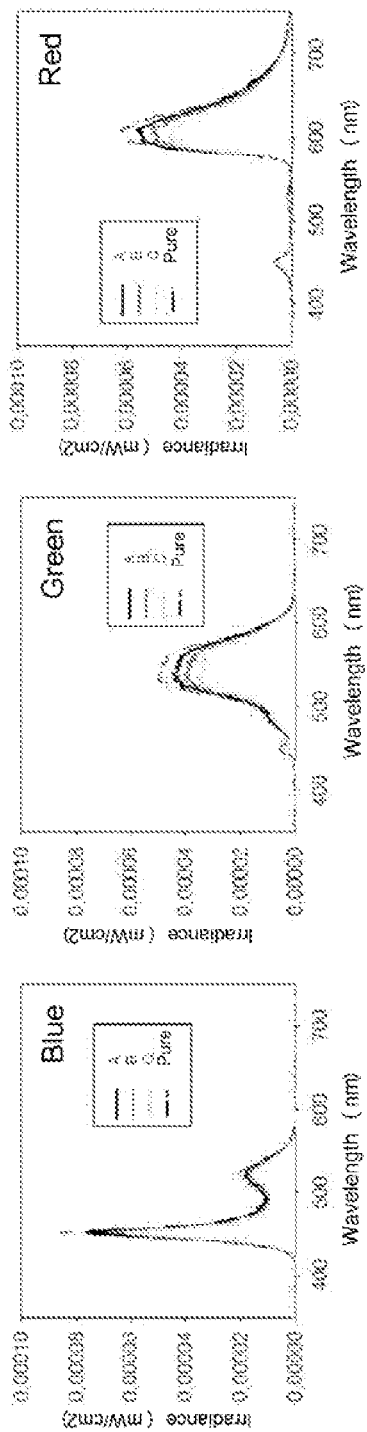
Figure 10D:
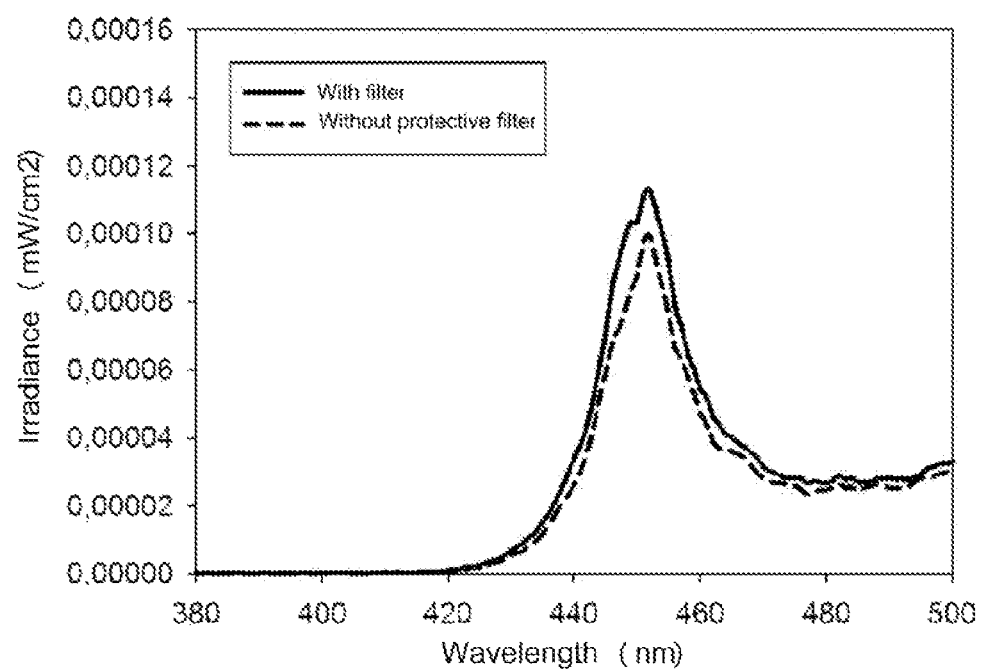

On the other hand in FIG. 10D, the irradiance (mW/cm$^2$) depending on the wavelength of the tablet Samsung Galaxy Tab 10.1 with and without the interposition of a protective filter which partially absorbs the short wavelengths of the visible spectrum, according to the object of the invention, is represented. In table 9, the represented values are indicated:

TABLE 9

| wavelength (nm) | Absorption of the filter (%) |
| --- | --- |
| 410 | 11 |
| 415 | 14 |
| 420 | 29 |
| 425 | 28 |
| 430 | 20 |
| 435 | 22 |
| 440 | 23 |
| 445 | 17 |
| 450 | 15 |
| 455 | 17 |
| 460 | 13 |
| 465 | 10 |
| 470 | 11 |
| 475 | 9 |
| 480 | 8 |
| 485 | 10 |
| 490 | 10 |
| 495 | 5 |
| 500 | 7 |

According to the results reported in all the previous tests, it is proved that the reduction in emission caused by LED-type displays on the spectrum between the 380-500 nm is beneficial and can be easily corrected also via hardware and software.

The invention claimed is:

1. A blocking element of short wavelengths in LED-type light sources comprising:
a substrate with a pigment distributed on its surface wherein
said pigment has an optical density such that it allows a selective absorption of light emission from LED-type light sources between a maximum percent of absorption and a minimum percent of absorption of wavelengths between 380 nm and 500 nm without completely blocking passage of the wavelengths between 380 nm and 500 nm, and wherein
said maximum percent of absorption is a sum of a predetermined maximum percent of absorption for each selected factor and
said minimum percent of absorption is a sum of predetermined minimum percent of absorption for each selected factor, wherein said each selected factor is at least one of:
the age of a user of LED-type light source,
the total exposure time of a user to the LED-type light source,
a lowest ambient lighting of a place where the user interacts with the LED-type light source,
the type of LED-type light source, and
a retinal or corneal disease state of the user, wherein
said pigment is evenly distributed over the surface of the substrate, and wherein the substrate comprises:
a multilayer substrate wherein at least one layer contains said pigment distributed over the surface of said layer; or
a coating containing said pigment in an entire coating.

2. The blocking element of short wavelengths according to claim 1 wherein the coating is one selected from gel, foam, emulsion, solution, dilution, or a combination thereof.

3. A LED display comprising the blocking element of short wavelengths according to claim 1.

4. A blocking method of short wavelengths in LED-type light sources characterized in that it comprises steps of:
selecting a mean optical density of a pigment between a maximum percent of absorption and a minimum percent of absorption in a range of wavelengths between 380 nm and 500 nm; and
pigmenting a substrate over its entire surface in such a way that the mean absorption is between said maximum and minimum percent of absorption without completely blocking passage of wavelengths between 380 nm and 500 nm; wherein
said maximum percent of absorption is a sum of a predetermined maximum percent of absorption for each selected factor and
said minimum percent of absorption is a sum of a predetermined minimum percent of absorption for each selected factor, wherein said each selected factor is at least one of:
an age of a user of LED-type light source,
a total exposure time of a user to the LED-type light source,
a lowest ambient lighting of a place where the user interacts with the LED-type light source,
the type of LED-type light source, and
a retinal or corneal disease state of the user; and wherein
said pigment is evenly distributed over the entire surface of the substrate.

5. A LED display obtained by a manufacturing process comprising a step of applying the method of claim 4.

* * * * *